(12) United States Patent
Grimm

(10) Patent No.: US 7,029,477 B2
(45) Date of Patent: Apr. 18, 2006

(54) SURGICAL INSTRUMENT AND POSITIONING METHOD

(75) Inventor: James E. Grimm, Winona Lake, IN (US)

(73) Assignee: Zimmer Technology, Inc., Chicago, IL (US)

(*) Notice: Subject to any disclaimer, the term of this patent is extended or adjusted under 35 U.S.C. 154(b) by 202 days.

(21) Appl. No.: 10/325,767

(22) Filed: Dec. 20, 2002

(65) Prior Publication Data

US 2004/0122436 A1 Jun. 24, 2004

(51) Int. Cl.
  *A61B 17/15* (2006.01)
(52) U.S. Cl. ........................................ 606/88
(58) Field of Classification Search .............. 606/86, 606/87, 88
  See application file for complete search history.

(56) References Cited

U.S. PATENT DOCUMENTS

| | | | |
|---|---|---|---|
| 4,524,766 A | 6/1985 | Petersen | |
| 4,759,350 A | 7/1988 | Dunn et al. | |
| 4,952,213 A | 8/1990 | Bowman et al. | |
| 5,007,936 A | 4/1991 | Woolson | |
| 5,230,338 A | 7/1993 | Allen et al. | |
| 5,251,127 A | 10/1993 | Raab | |
| 5,305,203 A | 4/1994 | Raab | |
| 5,451,228 A * | 9/1995 | Johnson et al. | 606/86 |
| 5,474,559 A | 12/1995 | Bertin et al. | |
| 5,484,446 A | 1/1996 | Burke et al. | |
| 5,486,180 A | 1/1996 | Dietz et al. | |
| 5,514,139 A | 5/1996 | Goldstein et al. | |
| 5,514,143 A | 5/1996 | Bonutti | |
| 5,551,429 A | 9/1996 | Fitzpatrick et al. | |
| 5,562,674 A | 10/1996 | Stalcup et al. | |
| 5,593,411 A | 1/1997 | Stalcup et al. | |
| 5,597,379 A | 1/1997 | Haines et al. | |
| 5,643,272 A | 7/1997 | Haines et al. | |
| 5,681,316 A | 10/1997 | DeOrio et al. | |
| 5,682,886 A | 11/1997 | Delp et al. | |

(Continued)

FOREIGN PATENT DOCUMENTS

DE 202 02 615 U 6/2002

(Continued)

OTHER PUBLICATIONS

NexGen Complete Knee Solution, Intramedullary Instrumentation Surgical Technique, For The NexGen Cruciate Retaining & Legacy Posterior Stabilized Knee, Zimmer, Inc. (1998).

(Continued)

*Primary Examiner*—David O. Reip
(74) *Attorney, Agent, or Firm*—Baker & Daniels LLP; Jonathan Feuchtwang (57) ABSTRACT

A surgical instrument having an anchoring member securable to an anatomical structure and an implement portion which is adjustably repositionable relative to the anchoring member. The implement portion is selectively translatably adjustable and selectively rotatably adjustable relative to the anchoring member. The implement portion may be selectively translatable along and/or selectively rotatable about at least two substantially perpendicular axes. The implement portion may be selectively translatable about three substantially perpendicular axes and/or selectively rotatable about three substantially perpendicular axes. The instrument may also include at least one reference element to facilitate the registration of the implement portion in a computer implemented guidance system. The reference element may be three non-linearly positioned elements disposed on a member which is removably mounted to the instrument. The implement portion may be a resection guide and the instrument may be used in the resection of a tibia when implanting a prosthetic knee joint.

21 Claims, 2 Drawing Sheets

U.S. PATENT DOCUMENTS

| | | | |
|---|---|---|---|
| 5,743,915 A | 4/1998 | Bertin et al. | |
| 5,755,803 A | 5/1998 | Haines et al. | |
| 5,810,827 A | 9/1998 | Haines et al. | |
| 5,871,018 A | 2/1999 | Delp et al. | |
| 5,879,354 A | 3/1999 | Haines et al. | |
| 5,904,691 A | 5/1999 | Barnett et al. | |
| 5,995,738 A | 11/1999 | DiGioia, III et al. | |
| 6,002,859 A | 12/1999 | DiGioia, III et al. | |
| 6,033,415 A | 3/2000 | Mittelstadt et al. | |
| 6,056,754 A | 5/2000 | Haines et al. | |
| 6,167,145 A | 12/2000 | Foley et al. | |
| 6,197,064 B1 | 3/2001 | Haines et al. | |
| 6,267,762 B1 * | 7/2001 | Millard et al. | 606/54 |
| 6,285,902 B1 | 9/2001 | Kienzle, III et al. | |
| 6,396,939 B1 | 5/2002 | Hu et al. | |
| 6,402,762 B1 | 6/2002 | Hunter | |
| 6,430,434 B1 | 8/2002 | Mittelstadt | |
| 6,450,978 B1 | 9/2002 | Brosseau et al. | |
| 6,477,400 B1 | 11/2002 | Barrick | |
| 6,514,259 B1 * | 2/2003 | Picard et al. | 606/88 |
| 6,551,325 B1 | 4/2003 | Neubauer et al. | |
| 6,554,837 B1 | 4/2003 | Hauri et al. | |
| 6,595,997 B1 | 7/2003 | Axelson, Jr. et al. | |
| 6,685,711 B1 * | 2/2004 | Axelson et al. | 606/88 |
| 6,695,848 B1 | 2/2004 | Haines et al. | |
| 6,712,824 B1 | 3/2004 | Millard et al. | |
| 2002/0068942 A1 | 6/2002 | Martin et al. | |
| 2002/0133160 A1 | 9/2002 | Axelson, Jr. et al. | |
| 2002/0133163 A1 | 9/2002 | Moctezuma | |
| 2003/0069585 A1 | 4/2003 | Axelson, Jr. et al. | |
| 2004/0039396 A1 | 2/2004 | Couture et al. | |
| 2005/0203528 A1 | 9/2005 | Couture et al. | |

FOREIGN PATENT DOCUMENTS

| | | | |
|---|---|---|---|
| EP | 0104732 A1 * | 4/1984 | 606/88 |
| FR | 2776176 A | 9/1999 | |

OTHER PUBLICATIONS

NexGen Complete Knee Solution, Posterior Reference, Multi-Referenceä 4-in-1 Femoral Instrumentation; Posterior Reference Surgical Technique, For NexGen Cruciate Retaining & Legacy Posterior Stabilized Knees, Zimmer, Inc. (1998).

NexGen Complete Knee Solution, Instrument Options, Surgeon-Specific, Zimmer, Inc. (believed to be at least as early as Nov. 2001).

Revision Knee Arthroplasty Surgical Guidelines, 2nd Edition, by Kelly Vince, M.D., John Insall, M.D., Robert Booth, Jr., M.D. and Giles Scuderi, M.D., Zimmer, Inc. (1999).

NexGen Complete Knee Solution, Micro-Mill Instrumentation Surgical Technique, For The NexGen Cruciate Retaining & Legacy Posterior Stabilized Knee, Zimmer, Inc. (1998).

NexGen Complete Knee Solution, Revision Instrumentation Surgical Technique for Legacy Knee Constrained Condylar Knee, Zimmer, Inc. (believed to be at least as early as Nov. 2001).

James E. Grimm et al., U.S Pat. App. entitled "Surgical Instrument and Method of Positioning Same" filed Dec. 20, 2002.

Nexgen Complete Knee Solution, Surgical Technique for Cruciate Retaining Knees Brochure (Jun. 1994).

Article—Computer Assisted Knee Replacement.

Article—Computer-Assisted Knee Surgical Total Replacement.

Article—A New Technique for Determining Proper Mechanical Axis Alignmetn During Total Knee Arthroplasty: Progress toward Computer-Assisted TKA.

* cited by examiner

FIG. 1

SURGICAL INSTRUMENT AND POSITIONING METHOD

BACKGROUND OF THE INVENTION

1. Field of the Invention

The present invention relates to surgical instruments and, more specifically, to a surgical guide and method for properly positioning a surgical instrument with respect to an anatomical structure.

2. Description of the Related Art

The controlled positioning of surgical instruments is of significant importance in many surgical procedures and various methods and guide instruments have been developed for properly positioning a surgical instrument. Such methods include the use of surgical guides which function as mechanical guides for aligning drilling or cutting instruments. The use of such surgical guides is common in orthopedic surgical procedures and such guides may be used to properly align a drill or cutting instrument with respect to a bone when preparing the bone for receiving an implant such as an artificial joint. Computer assisted surgical procedures which involve the image guidance of a surgical instrument are also known. Image guidance techniques typically involve acquiring preoperative images of the relevant anatomical structures and generating a data base which represents a three dimensional model of the anatomical structures. The relevant surgical instruments typically have a known and fixed geometry which is also defined preoperatively. During the surgical procedure, the position of the instrument being used is registered with the anatomical coordinate system and a graphical display showing the relative positions of the tool and anatomical structure may be computed in real time and displayed for the surgeon to assist the surgeon in properly positioning and manipulating the surgical instrument with respect to the relevant anatomical structure.

In image guided procedures, a robotic arm may be used to position and control the instrument, or, the surgeon may manually position the instrument and use the display of the relative position of the instrument and anatomical structure when positioning the instrument.

Although the known methods and instrumentation which are used to properly position surgical tools provide satisfactory results, the precision obtainable with image guided surgical methods often entails the use of expensive or cumbersome equipment which may limit the use of such methods.

SUMMARY OF THE INVENTION

The present invention provides a surgical instrument that includes an anchoring member and an implement portion that can be selectively repositioned relative to the anchoring member.

The invention comprises, in one form thereof, a surgical instrument for use with an anatomical structure. The instrument includes an anchoring member having a first portion securable to the anatomical structure and an instrument body having an implement portion. The implement portion is selectively translatable relative to the anchoring member along at least two substantially perpendicular translational axes. The implement portion is also selectively rotatable relative to the anchoring member about at least two substantially perpendicular rotational axes. The instrument includes at least one translation securement member for positively securing the implement portion in a selected translational position along one of the translational axes and at least one rotational securement member for positively securing the implement portion in a selected rotational position about one of the rotational axes.

The implement portion may be selectively translatable relative along three substantially mutually perpendicular translational axes and/or selectively rotatable about three substantially mutually perpendicular rotational axes. The surgical instrument may also include at least two translational securement members, each of the translational securement members positively securing the implement portion in a selected translational position along one of the translational axes. The surgical instrument may also include at least two rotational securement members, each of the rotational securement members positively securing the implement portion in a selected rotational position about one of the rotational axes.

The surgical instrument may also include at least one reference element registerable in a computer implemented image guidance system, the at least one reference element positioned at a predetermined orientation relative to the implement portion. The at least one reference element may take the form of at least three non-linearly positioned reference elements. The at least one reference element may be removeably mountable on the instrument and may take the form of at least three non-linearly positioned reference elements disposed on a reference member wherein the reference member is removeably mountable on the instrument at a predetermined orientation relative to the implement portion.

The surgical instrument may include first and second carriage portions wherein the first carriage portion is secured to the anchoring member with the first carriage portion and the anchoring member being relatively and selectively repositionable. The second carriage portion is secured to the first carriage portion with the second carriage portion and the first carriage portion being relatively and selectively repositionable. And, the implement portion is secured to the second carriage portion with the implement portion and the second carriage portion being relatively and selectively repositionable. The first portion of the anchoring member may be a threaded shaft engageable with the anatomical structure and the implement portion may be an instrument guide.

The present invention comprises, in another form thereof, a surgical instrument for use with an anatomical structure. The instrument includes an anchoring member having a first portion securable to the anatomical structure and an instrument body having an implement portion. The implement portion is selectively translatably adjustable and selectively rotatably adjustable relative to the anchoring member. The instrument also includes at least one reference element registerable in a computer implemented image guidance system wherein the at least one reference element is moved relative to the anchoring member by movement of the implement portion relative to the anchor member.

The implement portion may be selectively translatable along at least two substantially perpendicular translational axes and selectively rotatable about at least two substantially perpendicular rotational axes. The surgical instrument may also include at least one translation securement member for positively securing the implement portion in a selected translational position and at least one rotational securement member for positively securing the implement portion in a selected rotational position.

The implement portion may alternatively be selectively translatable along three substantially mutually perpendicular translational axes and selectively rotatable about three substantially mutually perpendicular rotational axes. The surgical instrument may also include at least two translation securement members, each such member positively securing the implement portion in a selected translational position along one of the translational axes and at least two rotational securement members, each such member securing the implement portion in a selected rotational position about one of the rotational axes.

The at least one reference element may take the form of at least three non-linearly positioned reference elements. The at least one reference element may be removeably mounted on the instrument at a predetermined orientation relative to the implement portion and may take the form of at least three non-linearly positioned reference elements disposed on a reference member wherein the reference member is removably mountable on the instrument at a predetermined orientation relative to the implement portion.

The present invention comprises, in yet another form thereof, a surgical instrument for resecting a tibia. The instrument includes an anchoring member having a first portion securable to the tibia and an instrument body having a resection guide. The resection guide is selectively translatable relative to the anchoring member and selectively rotatable relative to the anchoring member. The instrument further includes at least one reference element registerable in a computer implemented image guidance system and mounted in a predetermined orientation relative to the resection guide.

The at least one reference element may take the form of at least three non-linearly positioned reference elements mounted on a reference member wherein the reference member is removably mountable to the instrument in a known orientation relative to the resection guide. The instrument body may include a first carriage portion adjustably mounted on the anchoring member and a second carriage portion adjustably mounted on the first carriage portion with the resection guide being adjustably mounted on the second carriage portion. The first carriage portion may be rotatably mounted on the anchoring member, the second carriage portion may be rotatably and translatably mounted on the first carriage portion and the resection guide may be translatably mounted on the second carriage portion.

The present invention comprises, in another form thereof, a method of positioning a surgical instrument relative to an anatomical structure. The method includes providing an instrument having an anchoring member and a selectively repositionable implement portion and securing the anchoring member to the anatomical structure. The method also includes selectively adjusting the position of the implement portion relative to the anchoring member after securing the anchoring member to the anatomical structure. The selective adjustment of the implement portion includes selectively translating the implement portion along at least two substantially perpendicular axes and selectively rotating the implement portion about at least two substantially perpendicular axes.

The method may also include the step of registering the position of the implement portion in a computer implemented image guidance system after the step of securing the anchoring member. The step of registering the position of the implement portion may include removeably mounting at least three non-linearly positioned reference elements detectable by the computer implemented image guidance system on the instrument body.

The step of selectively adjusting the position of the implement portion may include selectively translating the implement portion along three substantially mutually perpendicular translational axes and/or selectively rotating the implement portion relative to the anchoring member about three substantially mutually perpendicular rotational axes.

The present invention comprises, in yet another form thereof, a method of positioning a surgical instrument with respect to an anatomical structure. The method includes providing an instrument having an anchoring member and a selectively repositionable implement portion and securing the anchoring member to the anatomical structure. The method also includes registering the position of the implement portion in a computer implemented image guidance system after the step of securing the anchoring member and selectively adjusting the position of the implement portion relative to the anchoring member. The selective adjustment of the implement portion includes positioning the implement portion in a selected translational position along at least one translational axis and positioning the implement portion in a selected rotational position about at least one rotational axis.

The step of selectively adjusting the position of the implement portion may involve securing the implement portion in the selected translational position and independently securing the implement portion in the selected rotational position.

The step of selectively adjusting the position of the implement portion may include positioning the implement portion in selected translational positions along at least two substantially perpendicular translational axes and/or positioning the implement portion in selected rotational positions about at least two substantially perpendicular rotational axes. Alternatively, the step of selectively adjusting the position of the implement portion may include positioning the implement portion in selected translational positions along three substantially mutually perpendicular translational axes and/or positioning the implement portion in selected rotational positions about three substantially mutually perpendicular rotational axes.

The present invention comprises, in another form thereof, a method of resecting a tibia. The method includes providing an instrument having an anchoring member and a resection guide and securing the anchoring member to the tibia. The method also includes registering the position of the resection guide in a computer generated guidance system after the step of securing the anchoring member and selectively adjusting the position of the resection guide relative to the anchoring member after the step of registering the position of the resection guide.

The step of selectively adjusting the position of the resection guide may also include securing the resection guide in the selected translational position and independently securing the resection guide in the selected rotational position. The method may also include the step of directly securing the resection guide to the tibia after the step of selectively adjusting the position of the resection guide.

The step of selectively adjusting the position of the resection guide may include positioning the resection guide in selected translational positions along at least two substantially perpendicular translational axes and positioning the resection guide in selected rotational positions about at least two substantially perpendicular rotational axes. Alternatively, the step of selectively adjusting the position of the resection guide may include positioning the resection guide in selected translational positions along three substantially mutually perpendicular translational axes and positioning the resection guide in selected rotational positions about three substantially mutually perpendicular rotational axes.

An advantage of the present invention is that it provides a surgical instrument which can be attached to an anatomical structure and has an implement portion which can be adjustably repositioned relative to the anatomical structure after attachment of the surgical instrument. The repositioning of the implement portion may be guided using a computer image guidance system and the invention thereby provides a highly adjustable, relatively small instrument which can be supportingly attached to the anatomical structure of interest and be used with a variety of computer implemented image guidance systems.

Another advantage is that it provides a surgical instrument which can be attached to an anatomical structure and has an implement portion which is adjustably repositionable relative to the anchoring member in a plurality of degrees of freedom. In some embodiments, the implement portion is adjustable about six degrees of freedom relative to the anchoring member.

Yet another advantage of the present invention is that it provides a surgical instrument that can be readily adjusted to properly position a resection guide when resecting a tibia to prepare the tibia for receiving the tibial implant of a prosthetic knee joint.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. Although the exemplification set out herein illustrates an embodiment of the invention, in one form, the embodiment disclosed below is not intended to be exhaustive or to be construed as limiting the scope of the invention to the precise form disclosed.

DESCRIPTION OF THE PRESENT INVENTION

Figure 1:
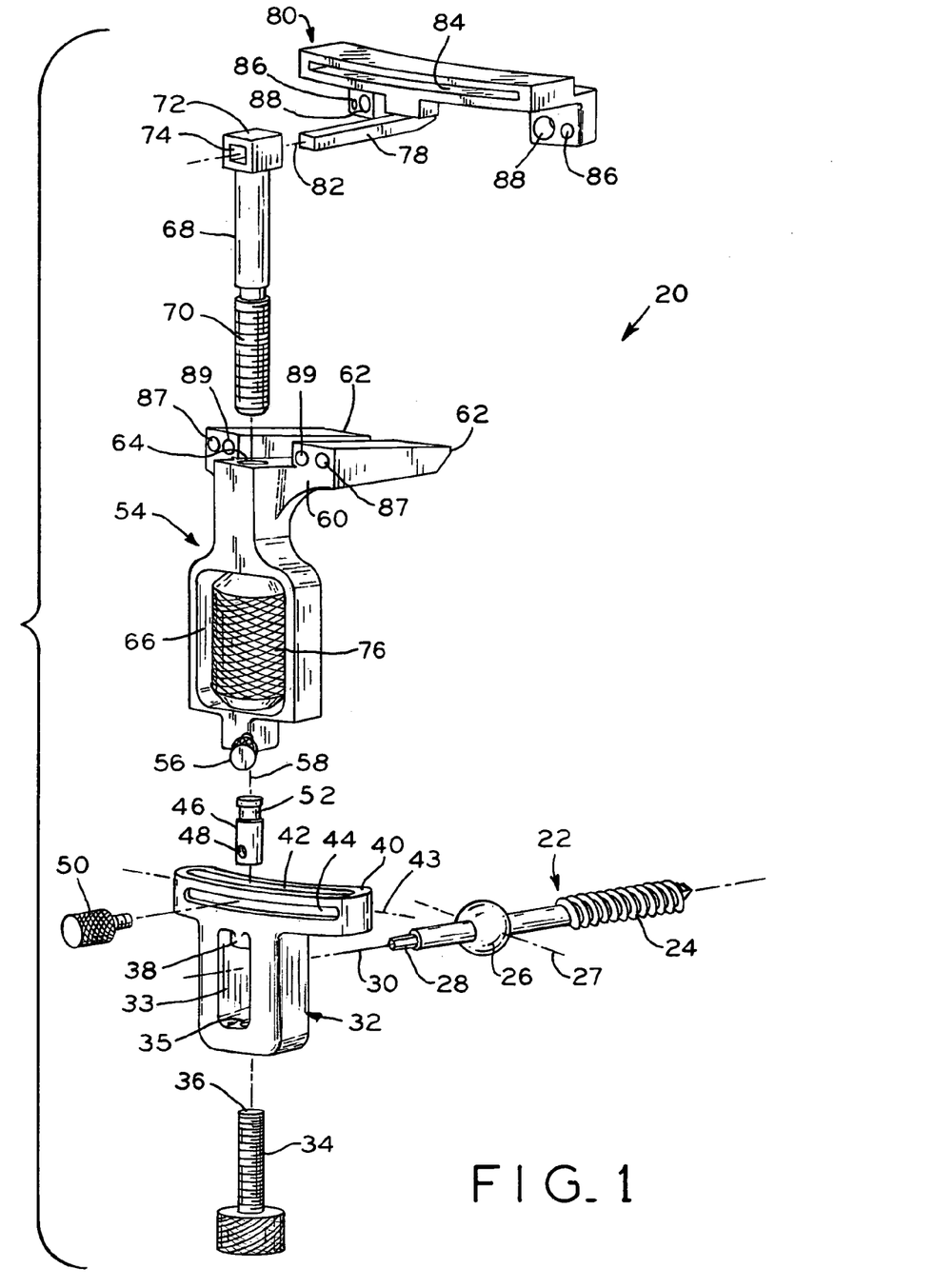
FIG. 1 is an exploded perspective view of a surgical instrument in accordance with the present invention.

In accordance with the present invention, a surgical instrument 20 is shown in FIG. 1. Instrument 20 includes an anchoring member 22 having a first portion which is securable to an anatomical structure which, in the illustrated embodiment, is threaded shaft 24. Anchoring member 22 also includes a spherical portion 26 and a hexagonal shaft portion 28. Anchoring member 22 defines an axis 30.

Instrument 20 also includes a first carriage body 32 which adjustably engages spherical portion 26 of anchoring member 22. Carriage body 32 has an adjustment member 34 which takes the form of a set screw in the illustrated embodiment for selectively engaging spherical portion 26. Set screw 34 is threadingly engaged with threaded opening 35 in carriage body 32. The distal end 36 of set screw 34 may have a surface defining a portion of a sphere having the same radius as spherical portion 26 to increase the surface area of engagement between set screw 34 and spherical porton 26. Spherical portion 26 is disposed between set screw 34 and seat 38 in opening 33 defined by carriage body 32. Firmly engaging set screw 34 with spherical portion 26 biases spherical portion 26 against seat 38 and secures spherical portion 26 in a desired orientation relative to carriage body 32 as discussed in greater detail below.

First carriage body 32 also includes an arcuate mounting portion 40 which defines a slot 42 having a transverse opening 44. Slide pin 46 is seated in slot 42 and can slide therein. Slide pin 46 includes a threaded opening 48 for receiving set screw 50. Set screw 50 projects through opening 44 to engage slide pin 46 and tightening of screw 50 secures slide pin 46 in a selected position in slot 42. An annular recess 52 is located near the end of slide pin 46 which projects outwardly from slot 42. Pin 46 is received in an opening in second carriage body 54 and is rotatable therein. A set screw 56 projects into annular recess 52 to secure pin 46 within second carriage body 54. When set screw 56 loosely engages slide pin 46, set screw 56 and second carriage body 54 are rotatable about axis 58 defined by slide pin 46. Firmly engaging set screw 56 with slide pin 46 secures set screw 56 and second carriage body 54 in a selected rotational position with respect to axis 58. Axis 58 is substantially perpendicular to axis 30 and when centrally located in slot 42 intersects axis 30.

A fork-shaped support structure 60 is located on the end of second carriage body 54 opposite sliding pin 46. When instrument 20 is attached to a tibia, distal ends 62 of support structure 60 may be placed in contact with the tibia to provide greater stability to attached instrument 20. Carriage body 54 includes a central, cylindrically shaped opening 64 which extends from proximate forked-shaped structure 60 to center void 66 defined by carriage body 54. Support shaft 68 has a threaded section 70 at one end and a head 72 defining a rectangular throughway 74 on its opposite end. Support shaft 68 extends through opening 64. Threaded section 70 is threadingly engaged with adjustment knob 76 which has a centrally located threaded bore and an outer knurled surface. The axis of shaft 68 and the bore defined by knob 76 extend coaxially with pin 46 and correspond to axis 58. Knob 76 is rotatable within void 66 but is not translatable along axis 58 and rotation of knob 76 translates shaft 68 along axis 58 by the relative rotation of threaded section 70 and the threaded bore of knob 76.

Mounted to shaft 68 is an implement portion 80 which includes a mounting member 78. Mounting member 78 has a rectangular cross section and is slidingly disposed in throughway 74. The non-circular cross-sectional shape of mounting member 78 and throughway 74 prevents mounting member 78 from rotating within throughway 74. Implement portion 80 can be selectively translated relative to mounting shaft 68 by sliding adjustment of member 78 within throughway 74 along axis 82 defined by member 78. Axis 82 is disposed substantially perpendicular to axis 58.

Implement portion 80 also includes a guide slot 84 which can be used to guide a cutting blade when resecting a proximal tibia to prepare the tibia for receiving a tibial implant forming a part of a prosthetic knee joint. Disposed proximate the opposite ends of guide slot 84, are two pairs of openings 86 and 88. When implement portion has been positioned in a desired location relative to the tibia, as discussed in greater detail below, headless pins may be inserted through openings 86 proximate the two opposed ends of slot 84 to firmly secure implement portion 80 to the tibia before resecting the tibia. Alternatively, openings 88 which are slightly larger than openings 86 may receive screws for firmly and directly securing implement portion 80 to the tibia. Similarly, openings 87, 89 in forked support structure 60 may receive pins or screws for securing support structure 60 to an anatomical structure.

Figures 2, 3, 4, 5, 6, 7:
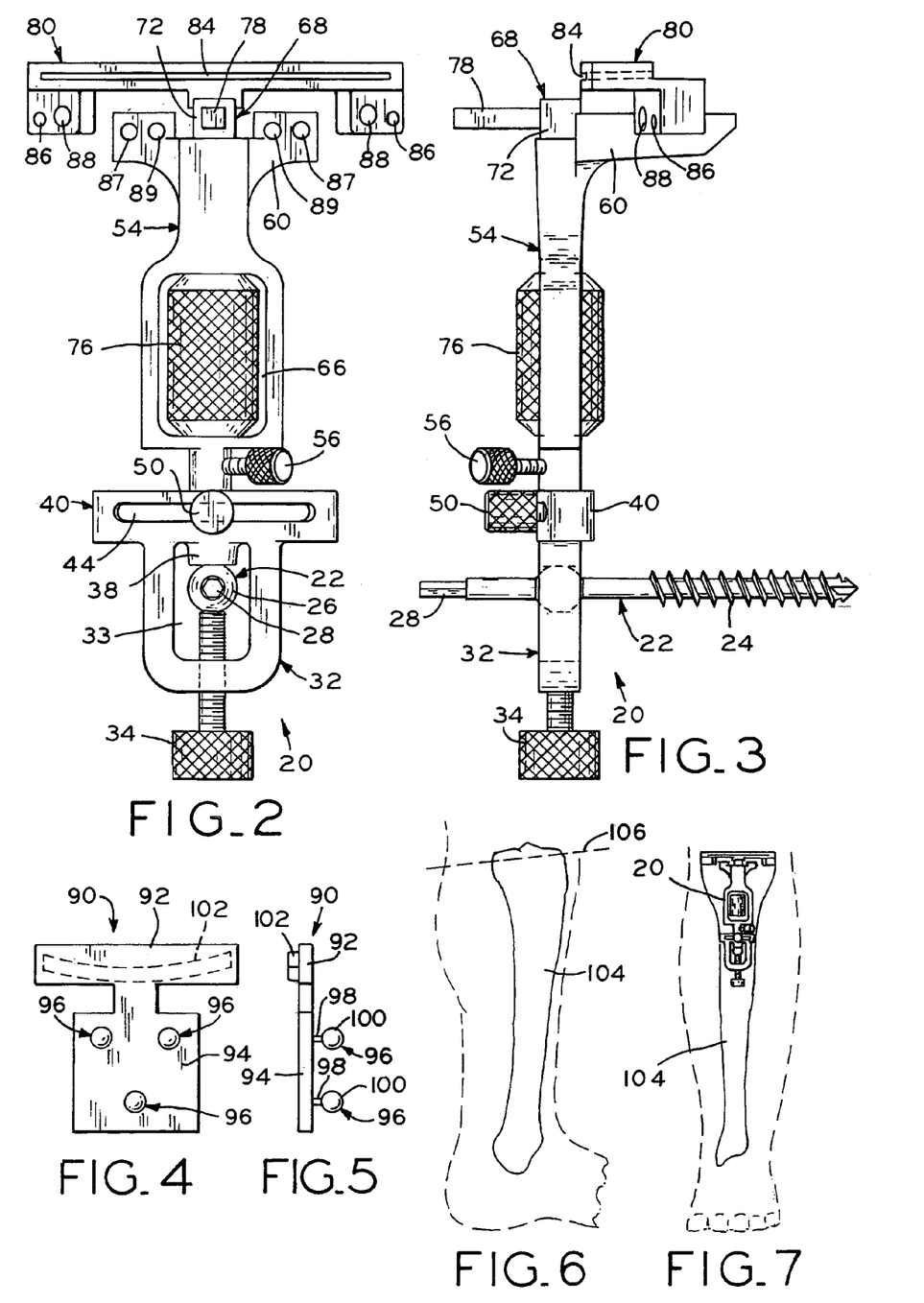
FIG. 2 is a front view of the surgical instrument of FIG. 1.
FIG. 3 is a side view of the surgical instrument of FIG. 1.
FIG. 4 is a view of a reference member.
FIG. 5 is a side view of the reference member of FIG. 4.
FIG. 6 is a view of a tibia.
FIG. 7 is a view of the surgical instrument of FIG. 1 attached to a tibia.

Reference member 90 is shown in FIGS. 4 and 5. Reference member 90 includes a mounting portion 92 and a registration portion 94. Mounted on registration portion 94 are a plurality of reference elements 96. In the disclosed embodiment, three non-linearly positioned reference elements 96 are mounted on reference member 90 and have a spherical portion 100 mounted on a post 98. Spherical portion 100 is a reflective structure which is used to reflect light to facilitate the detection and registration of reference elements 96 in a computer implemented image guidance system as discussed in greater detail below.

Reference member 90 is removably mountable to implement portion 80 by positioning mounting portion 92 in slot 84. Mounting portion 92 is configured to closely fit slot 84 so that mounting of reference member 90 will position reference elements 96 at known relative positions and orientations to implement portion 80. Reference member 90 may optionally include a projection 102 extending transverse to the length of mounting portion 92 and which abuts implement portion 80 adjacent slot 84 to facilitate the mounting of reference member 90 at a known and reproducible relative position to implement portion 80.

In alternative embodiments, reference elements 96 may be permanently secured to implement portion 80 or individually removably mounted to implement portion 80. Alternative reference elements may also include elements which emit a signal, such as an infrared emission, which is detectable by the computer implemented image guidance system, radio-opaque reference elements, and other types of reference elements known in the art. If radio-opaque reference elements are employed, reference member 90 may be formed of a radio-transparent material and advantageously positions reference elements 96 at a distance from the body of instrument 20 to limit the possibility of interference with the detection of the radio-opaque reference elements. In the illustrated embodiment, instrument 20 is manufactured of stainless steel, a radio-opaque material. In the illustrated embodiment, reference member 90 is an aluminum structure. The use of a removably mounted reference member 90 having reference elements 96 mounted thereon facilitates the use of instrument 20 with different types of image guidance systems by allowing different reference members having the same physical shape but with different types of reference elements to be used with a single instrument design.

The relevant dimensions of implement portion 80 and the location of reference elements 96 relative to implement portion 80 when reference member 90 is mounted to implement portion 80 can be determined in advance and this data may be entered into an image guidance system. The relevant dimensional data concerning the anatomical structure which is the subject of the surgical procedure may also be entered into the image guidance system in advance of the surgical procedure.

As is known in the art, the relevant dimensional data concerning an anatomical structure of interest, e.g., a tibia, may be determined using data acquired from images of the anatomical structure to generate a data base representing a model of the anatomical structure. The model of the anatomical structure may be a three dimensional model which is developed by acquiring a series of two dimensional images of the anatomical structure. Alternatively, the model of the anatomical structure may be a set of two dimensional images having known spatial relationships or other data structure which can be used to convey information concerning the three dimensional form of the anatomical structure. The model of the anatomical structure may then be used to generate displays of the anatomical structure from various perspectives for preoperative planning purposes and intraoperative navigational purposes. A variety of technologies may be employed to generate such a three dimensional model of an anatomical structure and include computed tomography (CT), magnetic resonance imaging (MRI), positron emission tomography (PET), ultrasound scanning and fluoroscopic imaging technologies.

The model of the anatomical structure obtained by such imaging technologies can be used for the intraoperative guidance of a surgical tool by facilitating the determination and display of the relative position and orientation of the surgical tool with respect to the actual anatomical structure. For example, if the model of the anatomical structure is a set of two dimensional images having known spatial relationships, several such images may be simultaneously displayed during the surgical procedure. By also displaying the position of the tool in the images and displaying images taken from different perspectives, e.g., one image facilitating the display of tool movement along the x and y coordinate axes and another image facilitating the display of tool movement along the z axis, the individual images may together represent the movement of the tool in three dimensions.

For reference purposes, a coordinate system defined by the actual anatomical structure which is the subject of interest will be referred to herein as the anatomical coordinate system and a coordinate system defined by the three dimensional model of the anatomical structure will be referred to as the image coordinate system. Data concerning the fixed size and shape of the surgical tool, or of a relevant portion thereof, which will be used in the image guided procedure is also determined pre-operatively to obtain a three dimensional model of the tool or the relevant portions thereof.

Rigid anatomical structures, such as skeletal elements, are well suited for such image guided surgical techniques and individual skeletal elements may be used to define separate coordinate systems. The different rigid structures, e.g., skeletal elements, may be subject to relative movement, for example, the femur and tibia of a patient may be relatively moved during the surgical procedure and separate three dimensional models and coordinate systems may be created for the different skeletal elements. During a knee replacement procedure, a three dimensional model of the tibia defining a first coordinate system may be utilized during the resection of the tibia while a separate coordinate system defined by a three dimension model of the femur may be utilized during the resection of the femur.

When conducting image guided surgical techniques, the image coordinate system is registered with the anatomical coordinate system and the position of the surgical tool is also registered with the image coordinate system. After the registration of both the actual anatomical structure and the surgical tool, the relative position and orientation of the surgical tool may be communicated to the surgeon by displaying together images of the anatomical structure and tool based upon the three dimensional models of the anatomical structure and tool which were previously acquired.

Computer implemented image guidance systems which provide for the registration of an actual anatomical structure with a three dimensional model representing that structure together with the registration or localization of a surgical tool within the image coordinate system to facilitate the display of the relative positions of the surgical tool and the actual anatomical structure are known in the art. Known methods of registering the anatomical structure with the image coordinate system include the use of implanted fiducial markers which are recognizable by one or more imaging technologies. Alternatively, implants may be located by physically positioning a digitizing probe or similar device in contact or at a known orientation with respect to the implant. Instead of using implants, it may also be possible to register the two coordinate systems by aligning anatomical landmark features.

Tracking devices employing various technologies enabling the registration or localization of a surgical tool and the tracking of the tool motion with respect to the anatomical coordinate system, which has been registered with the image coordinate system, are also known. For example, optical tracking systems which detect light either reflected from reflective targets or emitted by localizing emitters secured in a known orientation to the tool are known for determining the position of a surgical tool and registering the position of the tool within an image coordinate system representing a three dimensional model of an anatomical structure. Such a tracking system may take the form of a sensor unit having one or more lenses each focusing on separate charge coupled device (CCD) sensitive to infrared light. The sensor unit detects infrared light emitted by three or more non-linearly positioned light emitting diodes (LEDs) secured relative to the tool. A processor analyzes the images captured by the sensor unit and calculates the position and orientation of the tool. By registering the position of the sensing unit within the image coordinate system, the position of the tool relative to the anatomical structure, which has also been registered with the image coordinate system, may be determined and tracked as the tool is moved relative to the anatomical structure.

Alternative localizing systems may employ localizing emitters which emit an electromagnetic signal. It is also possible to employ digitizing physical probes which are brought into physical contact with the tool at predefined locations on the tool to register the position of the tool.

In the disclosed embodiment, the localizing system includes a light source and reference elements 96 reflect the light. The localizing system then detects the reflected light and computes the location of the individual reference elements 96 in a known manner. Reference elements 96 may be obtained from Northern Digital Inc. having a place of business at 103 Randall Dr., Waterloo, Onterio, Canada, N2V1C5. Other types of localizing systems may also be used with the present invention, such as those employing reference elements which emit a signal or which are radiopaque. Northern Digital Inc. supplies image guidance systems under the brand names Optotrak® and Polaris® which may be used with the present invention.

The use of instrument 20 in the resection of a proximal tibia will now be discussed. When implanting a prosthetic knee joint, the proximal tibia must be prepared to receive the tibial implant. The preparation of the proximal tibia typically involves resection of the tibial plateau leaving the proximal tibia with an inclined planar surface. The desired height and anterior/posterior angle of the planar surface defining the resected tibial plateau can be determined preoperatively and the location of this desired resection plane can be transformed into the image coordinate system and displayed with the three dimensional model of the tibia as is known in the art. FIG. 6 illustrates a tibia 104 and the location of a desired resection plane 106. FIG. 7 illustrates instrument 20 attached to tibia 104. An instrument which may be used to resect the femur is described in U.S. Patent Application Publication No. U.S. Ser. No. 2004/0122305 A1, entitled SURGICAL INSTRUMENT AND METHOD OF POSITIONING SAME, filed on Dec. 20, 2002, and published on Jun. 24, 2004, which is expressly incorporated herein by reference.

Instrument 20 is secured to tibia 104 by first securing anchoring member 22 to tibia 104. Implement portion 80 is then adjustably repositioned relative to anchoring member 22 to align slot 84 with resection plane 106. Implement portion 80 is adjustably repositionable relative to anchoring member 22 in all six degrees of freedom, i.e., it may be translatably adjusted along three substantially perpendicular axes and rotatably adjusted about three substantially perpendicular axes. This freedom of movement allows anchoring member 22 to be secured to tibia 104 anywhere within the general area which still permits the resection guide, i.e., slot 84 to be positioned in a coplanar relationship to desired resection plane 106.

The order in which the different adjustments of implement portion 80 are made after securing anchoring member 22 to tibia 104 can vary and, if necessary or desirable, may be an iterative process. For example, several coarse adjustments could be initially made to place implement portion 80 approximately into its correct position, then reference member 90 could be registered in the computer image guidance system and implement portion 80 then further adjusted as necessary to align slot 84 with the desired resection plane 106. In one sequence of adjustment, the first adjustment is to properly position instrument 20 about the rotational axis 30 defined by anchoring member 22. When instrument 20 is positioned in the proper orientation about axis 30, the relevant rotational securement member, i.e., set screw 34, is tightened to secure the relative positions of spherical portion 26 and carriage body 32. Next, the translational position of carriage body 54 relative to anchoring member 22 along axis 43 defined by slot 42 is adjusted to position implement portion 80 in the desired position. Although slot 42 is slightly arcuate, the curvature of slot 42 is slight and slot 42 defines a translational axis 43 which is substantially mutually perpendicular to translational axes 58 and 82. When implement portion 80 is in its selected translational position along axis 43, the relevant translation securement member, i.e., set screw 50, is tightened to secure the relative positions of pin 46 and carriage body 32.

The rotational position of implement portion 80 about axis 58 is then set by loosening the relevant rotational securement member, i.e., set screw 56, adjustably repositioning carriage body 54 and implement portion 80 to place implement portion 80 into its desired rotational position about axis 58 and retightening set screw 56. The height of the resection is then set by rotating the relevant translational securement member, i.e., knob 76, to selectively translate support shaft 68 along axis 58. The anterior/posterior slope of the resection may then be set by rotating instrument 20 about spherical portion 26 about a rotational axis 27 which is substantially mutually perpendicular to rotational axes 30 and 58. The rotation about axis 27 is accomplished by loosening set screw 34, repositioning instrument 20 and retightening set screw 34. The relative rotation of instrument 20 about spherical portion 26 is not limited to axis 27 when loosening set screw 34 and rotation about axes 30 and 58 is also possible when loosening set screw 34.

After slot 84 has been positioned in alignment with desired resection plane 106, implement portion 80 is translated along axis 82 by sliding implement portion 80 relative to support shaft 68 until implement portion 80 contacts tibia 104. Implement portion 80 is then secured directly to tibia 104 by placing headless pins in tibia 104 through openings 86 or by securing screws to tibia 104 through openings 88. After firmly securing implement portion 80 directly to tibia 104, the resection guide formed by slot 84 is used to guide a cutting blade in the resection of tibia 104. In an alternative embodiment, implement portion 80 may define a milling guide to facilitate the resection of tibia 104. Implement portion 80 may also be adapted for use in other surgical procedures and/or perform an alternative function, e.g., provide a drill guide.

While this invention has been described as having an exemplary design, the present invention may be further modified within the spirit and scope of this disclosure. This application is therefore intended to cover any variations, uses, or adaptations of the invention using its general principles.

What is claimed is:

1. A surgical instrument for use with an anatomical structure, said instrument comprising:
    an anchoring member having a first portion securable to the anatomical structure;
    an implement portion, wherein said implement portion is selectively translatable along three substantially mutually perpendicular translational axes and said implement portion is selectively rotatable relative to said anchoring member about at least two substantially perpendicular rotational axes;
    at least one translational securement member for positively securing said implement portion in a selected translational position along one of said translational axes; and
    at least one rotational securement member for positively securing said implement portion in a selected rotational position about one of said rotational axes.

2. The surgical instrument of claim 1 wherein said implement portion is selectively rotatable about three substantially mutually perpendicular rotational axes.

3. The surgical instrument of claim 2 wherein said at least one translational securement member comprises at least two translational securement members, each of said translational securement members positively securing said implement portion in a selected translational position along one of said translational axes.

4. The surgical instrument of claim 2 wherein said at least one rotational securement member comprises at least two rotational securement members, each of said rotational securement members positively securing said implement portion in a selected rotational position about one of said rotational axes.

5. The surgical instrument of claim 1 further comprising at least one reference element registerable in a computer implemented image guidance system, said at least one reference element positioned at a predetermined orientation relative to said implement portion.

6. The surgical instrument of claim 5 wherein said at least one reference element comprises at least three non-linearly positioned reference elements.

7. The surgical instrument of claim 5 wherein said at least one reference element is removeably mountable on said instrument at a predetermined orientation relative to said implement portion.

8. The surgical instrument of claim 5 wherein said at least one reference element comprises at least three non-linearly positioned reference elements disposed on a reference member, said reference member being removably mountable on said instrument at a predetermined orientation relative to said implement portion.

9. The surgical instrument of claim 1 further comprising first and second carriage portions, said first carriage portion secured to said anchoring member wherein said first carriage portion and said anchoring member are relatively and selectively repositionable; said second carriage portion secured to said first carriage portion wherein said second carriage portion and said first carriage portion are relatively and selectively repositionable; said implement portion secured to said second carriage portion wherein said implement portion and said second carriage portion are relatively and selectively repositionable.

10. The surgical instrument of claim 9 wherein said first portion of said anchoring member comprises a threaded shaft engageable with the anatomical structure and said implement portion comprises an instrument guide.

11. A surgical instrument for use with an anatomical structure, said instrument comprising:
    an anchoring member having a first portion securable to the anatomical structure;
    an implement portion, said implement portion being selectively translatably adjustable and selectively rotatably adjustable relative to said anchoring member; and
    at least one reference element registerable in a computer implemented image guidance system wherein said at least one reference element is moved relative to said anchoring member by movement of said implement portion relative to said anchoring member;
    wherein said implement portion is selectively translatable along three substantially mutually perpendicular translational axes and said implement portion is selectively rotatable about three substantially mutually perpendicular rotational axes.

12. The surgical instrument of claim 11 further comprising at least one translation securement member for positively securing said implement portion in a selected translational position and at least one rotational securement member for positively securing said implement portion in a selected rotational position.

13. The surgical instrument of claim 11 further comprising:
    at least one translation securement member for positively securing said implement portion in a selected translational position along one of said translational axes; and
    at least one rotational securement member for positively securing said implement portion in a selected rotational position about one of said rotational axes.

14. The surgical instrument of claim 11 further comprising:
    at least two translation securement members, each of said translational securement members positively securing said implement portion in a selected translational position along one of said translational axes; and
    at least two rotational securement members, each of said rotational securement members positively securing said implement portion in a selected rotational position about one of said rotational axes.

15. The surgical instrument of claim 11 wherein said at least one reference element comprises at least three non-linearly positioned reference elements.

16. The surgical instrument of claim 11 wherein said at least one reference element is removably mountable on said instrument at a predetermined orientation relative to said implement portion.

17. The surgical instrument of claim 11 wherein said at least one reference element comprises at least three non-linearly positioned reference elements disposed on a reference member, said reference member being removably mountable on said instrument at a predetermined orientation relative to said implement portion.

18. A surgical instrument for resecting a tibia, said instrument comprising:
a fastener selectively secured to the tibia;
a resection guide, said resection guide being selectively translatable relative to said fastener and selectively rotatable relative to said fastener; and
at least one reference element registerable in a computer implemented image guidance system, said at least one reference element mounted in a predetermined orientation relative to said resection guide.

19. The instrument of claim 18 wherein said at least one reference element comprises at least three non-linearly positioned reference elements mounted on a reference member, said reference member being removably mountable to said instrument in a known orientation relative to said resection guide.

20. The instrument of claim 18, further comprising:
a first carriage portion adjustably mounted on said fastener; and
a second carriage portion adjustably mounted on said first carriage portion, said resection guide being adjustably mounted on said second carriage portion.

21. The instrument of claim 20 wherein said first carriage portion is rotatably mounted on said fastener, said second carriage portion is rotatably and translatably mounted on said first carriage portion and said resection guide is translatably mounted on said second carriage portion.

* * * * *